US011421218B2

(12) United States Patent
D'Andrea et al.

(10) Patent No.: US 11,421,218 B2
(45) Date of Patent: Aug. 23, 2022

(54) METHODS FOR ENHANCING THE EFFICIENCY OF GENE EDITING

(71) Applicants: Dana-Farber Cancer Institute, Inc., Boston, MA (US); Oregon Health & Science University, Portland, OR (US)

(72) Inventors: Alan D'Andrea, Winchester, MA (US); Markus Grompe, Portland, OR (US)

(73) Assignees: Dana-Farber Cancer Institute, Inc., Boston, MA (US); Oregon Health & Science University, Portland, OR (US)

( * ) Notice: Subject to any disclaimer, the term of this patent is extended or adjusted under 35 U.S.C. 154(b) by 792 days.

(21) Appl. No.: 16/086,559

(22) PCT Filed: Mar. 23, 2017

(86) PCT No.: PCT/US2017/023828
§ 371 (c)(1),
(2) Date: Sep. 19, 2018

(87) PCT Pub. No.: WO2017/165655
PCT Pub. Date: Sep. 28, 2017

(65) Prior Publication Data
US 2019/0085315 A1 Mar. 21, 2019

Related U.S. Application Data

(60) Provisional application No. 62/312,300, filed on Mar. 23, 2016.

(51) Int. Cl.
*C12N 15/10* (2006.01)

(52) U.S. Cl.
CPC .................. *C12N 15/102* (2013.01)

(58) Field of Classification Search
None
See application file for complete search history.

(56) References Cited

U.S. PATENT DOCUMENTS

| | | | |
|---|---|---|---|
| 5,176,996 A | 1/1993 | Hogan et al. |
| 5,422,251 A | 6/1995 | Fresco |
| 5,585,245 A | 12/1996 | Johnsson et al. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,200,759 B1 | 3/2001 | Dove et al. |
| 6,453,242 B1 | 9/2002 | Eisenberg et al. |
| 6,534,261 B1 | 3/2003 | Cox, III et al. |
| 2005/0064474 A1 | 3/2005 | Urnov et al. |
| 2007/0218528 A1 | 9/2007 | Miller |
| 2008/0131962 A1 | 6/2008 | Miller |
| 2011/0201055 A1 | 8/2011 | Doyon et al. |
| 2011/0301073 A1 | 12/2011 | Gregory et al. |

FOREIGN PATENT DOCUMENTS

| | | |
|---|---|---|
| WO | WO 1995/019431 | 7/1995 |
| WO | WO 1996/006166 | 2/1996 |
| WO | WO 1998/044350 | 10/1998 |
| WO | WO 1998/053057 | 11/1998 |
| WO | WO 1998/053058 | 11/1998 |
| WO | WO 1998/053059 | 11/1998 |
| WO | WO 1998/053060 | 11/1998 |
| WO | WO 1998/054311 | 12/1998 |
| WO | WO 2000/27878 | 5/2000 |
| WO | WO 2001/060970 | 8/2001 |
| WO | WO 2001/088197 | 8/2001 |
| WO | WO 2002/016536 | 2/2002 |
| WO | WO 2002/099084 | 12/2002 |
| WO | WO 2003/016496 | 2/2003 |
| WO | WO 2010/065123 A1 | 6/2010 |
| WO | WO 2014/093595 A1 | 6/2014 |
| WO | WO 2014/099744 A1 | 6/2014 |
| WO | WO 2015/079056 A1 | 6/2015 |

OTHER PUBLICATIONS

Adamson, B. et al., "A genome-wide homologous recombination screen identifies the RNA-binding protein RBMX as a component of the DNA-damage response," Nature Cell Biology, 14(3): 318-328; Supplementary Information DOI: 10.1038/ncb2426, 15 pages.
Beerman, I. et al., "Quiescent Hematopoietic Stem Cells Accumulate DNA Damage during Aging that is Required upon Entry into Cell Cycle," Cell Stem Cell, 15: 37-50 (2014).
Budke, B. et al., "RI-1: a chemical inhibitor of RAD51 that disrupts homologous recombination in human cells," Nucleic Acids Research, 40(15): 7347-7357 (2012).
Certo, M. et al., "Tracking genome engineering outcome at individual DNA breakpoints," Nature Methods, 8(8): 671-676 (2011).
Huang, F. et al., "Inhibition of Homologous Recombination in Human Cells by Targeting RAD51 Recombinase," Journal of Medicinal Chemistry, 55: 3011-3020 (2012).
Zhang, H. et al., "Bone Marrow Failure in Fanconi Anemia from Hyperactive TGF-β Signaling," Blood, 124(21), 56th Annual Meeting of the American Society of Hematology, 5 pages (Dec. 6-9, 2014).
Zhang, H. et al., "TGF-β Inhibition Rescues Hematopoietic Stem Cell Defects and Bone Marrow Failure in Fanconi Anemia," Cell Stem Cell, 18(5): 668-681 (2016).
Anguela et al., "Robust ZFN-mediated genome editing in adult hemophilic mice," Blood, Nov. 2013, 122(19):3283-3287.
Azuma et al., "Robust expansion of human hepatocytes in Fah-/-/Rag2-/-/Il2rg-/- mice," Nature Biotechnology, 2007, 25(8):903-910.
Fields et al., "A novel genetic system to detect protein-protein interactions," Nature, Jul. 1989, 340:245-246.
Li et al., "In vivo genome editing restores haemostasis in a mouse model of haemophilia," Nature, Jun. 2011, 475(7355):217-221.
Lisowski et al., "Selection and evaluation of clinically relevant AAV variants in a xenograft liver model," Nature, Dec. 2013, 506(7488):382-386.
Paulk et al., "AAV-Mediated Gene Targeting Is Significantly Enhanced by Transient Inhibition of Nonhomologous End Joining or the Proteasome In Vivo," Human Gene Therapy, Apr. 2012, 23(6):658-665.

(Continued)

*Primary Examiner* — Kagnew H Gebreyesus
(74) *Attorney, Agent, or Firm* — Fish & Richardson P.C.

(57) ABSTRACT

The present invention provides methods of increasing the efficiency of genome editing.

7 Claims, 17 Drawing Sheets

(56) References Cited

OTHER PUBLICATIONS

Paulk et al., "Adeno-Associated Virus Gene Repair Corrects a Mouse Model of Hereditary Tyrosinemia In Vivo," Hepatology, Mar. 2010, 51(4):1200-1208.
PCT International Preliminary Report on Patentability in International Appln. No. PCT/US2017/023828, dated Sep. 25, 2018, 9 pages.
PCT International Search Report and Written Opinion in International Appln. No. PCT/US2017/023828, dated May 19, 2017, 15 pages.
PCT Invitation to Pay Additional Fees International Appln. No. PCT/US2017/023828, dated Jun. 9, 2017, 14 pages.

METHODS FOR ENHANCING THE EFFICIENCY OF GENE EDITING

RELATED APPLICATIONS

This application is a U.S. National Phase application, filed under 35 U.S.C. § 371, of International Application No. PCT/US2017/023828, filed on Mar. 23, 2017, which claims priority to and the benefit of U.S. Ser. No. 62/312,300, filed Mar. 23, 2016, the contents of which are incorporated herein by reference in their entireties.

GOVERNMENT INTEREST

This invention was made with government support under DK048252 awarded by the National Institutes of Health. The government has certain rights in the invention.

FIELD OF THE INVENTION

The present invention relates generally to the enhancement of genome manipulation by targeted nuclease by shifting the balance of DNA repair mechanisms.

BACKGROUND OF THE INVENTION

Genome engineering is a powerful tool for dissecting biological mechanisms. The ability to precisely edit genomes has expanded significantly in recent years with the development of sequence-directed nucleases that can generate targeted double-strand breaks (DSBs) in DNA Chromosomal DSBs trigger DNA repair via two cellular pathways that can be harnessed for genome editing. Nonhomologous end joining (NHEJ) is an error-prone ligation process that can result in small insertions and deletions (indels) at cleavage sites. By targeting open reading frames, this pathway can be used to disrupt genes through frame-shifting mutations. Homologous recombination or homology-directed repair (HR or HDR) employs homologous DNA sequences as templates for precise repair. By supplying a donor repair template, this pathway can be exploited to precisely edit genomic sequence or insert exogenous DNA. Zinc-finger nucleases (ZFNs) and transcription activator-like effector nucleases (TALENs) are sequence-directed nucleases that, in pairs, can generate targeted DSBs and have shown promise as genome engineering tools. However, ZFN and TALEN proteins must be custom designed for each genome modification—a costly and uncertain process. In contrast, in the CRISPR/Cas9 system, a common nuclease, Cas9, is directed to targeted loci through simple base pairing by a small RNA molecule. With the ease of producing a targeting RNA, the CRISPR/Cas9 system promises to transform gene editing.

Nearly all the work conducted to date has taken advantage of aberrant NHEJ to generate frameshifting mutations in open reading frames. While this is an effective approach for disrupting gene function, it is stochastic and limited to the generation of indels. NHEJ does not permit the precise incorporation of exogenous DNA, including visual markers to aid in screening, and thus its application is limited. Further, more complex genome engineering applications such as the incorporation of recombination sites for making conditional alleles, endogenous protein tagging, or precise editing of genomic sequences require HR. Here we present tools and techniques that overcome these limitations by shifting the balance between NHEJ and HR in favor of HR resulting in more efficient recombination of the donor DNA with the target locus.

SUMMARY OF THE INVENTION

In various aspects, the invention features methods for increasing the efficiency of genome editing by contacting a cell undergoing genome editing with a compound that inhibits the expression or activity of TGFβ.

In other aspects, the invention features methods for increasing homologous recombination DNA repair of a targeted DNA double strand break in a cell by contacting the cell with a compound that inhibits the expression or activity of TGFβ.

The cell is a differentiated cell. Alternatively the cell is a primary cell.

The cell is contacted in vivo or in vitro. For example, the cell is contacted in vivo in a mammalian subject. Examples of a mammalian subject include, but are not limited to, a human, a cow, a sheep, a horse, a pig, a dog, a cat, a monkey, a guinea pig, and a rat. The cell is contacted with the compound before, during or after the cell undergoes genome editing. For example, the cell is contacted with the compound at least 1 day before the genome editing. Optionally, the cell is contacted with the compound at least 10 day after the genome editing. In some aspects the compound is administered systemically.

In other aspects, the method further comprises contacting the cell with a KU70 inhibitor or a DNA ligase IV inhibitor.

The compound is a nucleic acid, an antibody or a small molecule. The nucleic acid is an shRNA, siRNA or an sgRNA specific for TGFβ, SMAD2, SMAD3, or 15-PGDH.

Preferably the antibody is specific for TGFβ or TGFβR1. The small molecule is a DNA dependent protein kinase inhibitor, a SMAD3 inhibitor, a 15-PGDH inhibitor, a TGFβR1 inhibitor, an AT1 antagonist or a MEK1/2 inhibitor.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 2A is a graph showing that TGF-β pathway inhibition induces expression of the majority genes involved in DNA damage repair in HSCs from WT mice. HSCs were sorted front WT mice after 48 h treatment with TGF-β or isotype control antibody, and used for qRT-PCR analysis.

FIG. 2B is a graph showing that the expression levels of DNA damage repair genes in Fancd2−/− and WT HSCs. Some genes involved in HR and NHEJ pathways were pointed out by arrow.

FIG. 2C is a graph showing that blockade of TGF-β pathway induces HR gene expression and downregulates NHEJ gene expression in HSCs from Fancd2−/− mice. HSCs were sorted from Fancd2−/− mice after 48 h treatment with TGF-β or isotype control antibody, and used for qRT-PCR analysis. Some genes involved in HR and NHEJ pathways were pointed out by arrow.

FIGS. 2D-2E are graphs showing gene expression of representative NHEJ (FIG. 2D) and HR (FIG. 2E) genes Lig4, Prkdc, Brca2, and Xrcc1 in HSCs.

FIG. 2F is a graph showing the frequency of HSCs in Fancd2−/− mice after 48 h treatment with TGF-β or isotype control antibody (n=4 mice per group).

FIG. 2G is a schematic of acetaldehyde sensitivity assay in bone marrow HSPCs from WT or Fancd2−/− mice.

FIG. 2H is a graph showing that TGF-β antibody does not protect the Fancd2−/− HSPCs from genotoxic stress when HR is inhibited. HSPCs from WT or Fancd2−/− mice were exposed to TGF-β antibody and RAD51 inhibitors (10 μM) for 30 min followed by exposure to acetaldehyde for 4 hrs. The cells were then washed and cultured in presence of TGF-β antibody and RAD51 inhibitors for five days and survival was determined. Error bars represent mean±s.e.m. *p<0.05; **p<0.01. See also FIGS. 3A-3H.

FIG. 3A is an experimental scheme for inhibition of TGF-β Pathway in mice. WT or Fancd2−/− mice were treated with isotype or TGF-β antibody (10 mg/kg) for 48 h, and bone marrow HSCs were sorted for gene expression profile and cell cycle analysis.

FIG. 3B shows an increased number of Fancd2−/− HSCs in S-G2M phase of cell cycle after 1D11 treatment. Cell cycle analysis of HSCs from WT or Fancd2−/− mice treated with isotype or TGF-β antibody for 48 h is shown. (n=4 mice per group).

FIG. 3C is representative immunoblots showing TGF-β antibody efficiently inhibits the level of p-Smad2 in hematopoietic progenitors from Fancd2−/− mice.

FIG. 3D is a graph showing that RAD51 inhibitors, RI-1 and B02, significantly decrease HR efficiency. Homologous recombination assay was measured in U2OS cells with DR-GFP reporter after treatment with 10 μM RI-1 and 10 μM B02. The representative of two independent experiments is presented.

FIGS. 3E and 3F are graphs showing that RAD51 inhibitors, RI-1 and B02, efficiently block RAD51 foci formation. GM6914 (FA-A) cells or corrected GM6914+FANCA cells were treated with 1 μMMMC and 10 μM inhibitors for 6 h before immunofluorescence analysis. Representative images (FIG. 3E) and quantification (FIG. 3F) of RAD51 foci are shown, (Scale bar: 50 μm).

FIG. 3G is a graph showing that RAD51 inhibitors do not show cytotoxicity in HSPCs. HSPCs from WT or Fancd2−/− mice were treated with B02 (10 μM) or RI-1 (10 μM) in vitro for five days and survival was determined.

FIG. 3H is a graph of colony forming assay showing that RAD51 inhibitors block the protective function of TGF-β antibody after genotoxic stress in Fancd2−/− HSPCs. HSPCs from WT or Fancd2−/− mice were exposed to TGF-β antibody (10 μg/mL) and RAD51 inhibitors (10 μM) for 30 min followed by exposure to acetaldehyde for 4 hrs. The cells were then washed and cultured in presence of TGF-β antibody and RAD51 inhibitors for 7-9 days, and hematopoietic colonies were counted. Error bars represent mean±s.e.m.

FIGS. 4A-4B are graphs showing that TGF-β pathway inhibition affects the choice of HR versus NHEJ pathways in repairing individual DNA breakpoints in FA cells. GM6914 cells (FA-A cells) or FANCA corrected GM6914 cells with shControl or shSMAD3 were used to generate traffic light reporter system, and then were infected with GFP-donor template and I-SceI lentivirus to generate DNA breakpoints. Quantification analysis of HR and NHEJ repair events is shown. (FIG. 4B) The ratio of HR to NHEJ activity based on the data in (FIG. 4A).

FIG. 4C is a graph showing that SD208 mediated TGF-β pathway inhibition increases FIR events and decreases NHEJ events. Quantification of HR and NHEJ repair events in GM6914 cells exposed to SD-208 for 72 hrs as detected by traffic light reporter assay described in FIG. 4A.

FIG. 4D is a graph showing that SMAD3 knockdown significantly increases HR efficiency. HR assay was measured in U2OS cells with DR-GFP reporter after transduction with lentivirus encoding indicated shRNAs. The representative of three independent experiments is presented.

FIG. 4E is a graph of an NHEJ reporter assay showing decreased NHEJ activity in U2OS cells after inhibition of the TGF-β pathway by small molecule inhibitors.

FIGS. 4F and 4G are graphs showing that TGF-β pathway inhibition promotes HR activity in FA cells. Representative images (FIG. 4F) and quantification (FIG. 4G) of RAD51 foci in MMC treated GM6914 (FA-A) cells or FANCAcorrected GM6914 cells with shRNA-mediated knockdown of SMAD3. Cells were exposed tot mM MMC for 6 h, and allowed to recover for 24 h and 48 h. RAD51 foci were then identified. One hundred cells were scored for RAD51 foci. (Scale bar: 20 μm) Error bars represent mean±s.e.m. See also FIGS. 5A-5D.

FIG. 5A is a schematic of traffic light reporter assay. Endonuclease 1-SceI induces double strand break (DSB) in the restriction site. If the DSB is repaired by HR using truncated GFP template, the full eGFP gets reconstituted and cells are GFP-positive; if the DSB is repaired by NHEJ, 2 bp frameshift leads to T2A and mCherry sequences in frame, and cells are mCherry-positive.

FIG. 5B is a graph showing HR and NHEJ repair analyzed by traffic light reporter (TLR) system. GM6914 (FA-A cells) or FANCA corrected GM6914 cells with shControl or shSMAD3 were infected with lentivirus encoding TLR-BFP reporter and were then infected with and I-SceI only encoding lentivirus to generate DNA breakpoints. HR and NHEJ repair events (GFP or mCherry positive cells) were quantified by flow cytometry.

FIG. 5C are graphs of immunoblots with the indicated antibodies of the lysates from GM6914 (FA-A) cells or FANCA-corrected GM6914 cells with shRNA-mediated knockdown of SMAD3. Cells were exposed to 1 M MMC for 8 h and allowed to recover for 24 and 48 hours.

FIG. 5D is a graph of analysis of siRNA screening data showing that siRNA mediated knockdown of the majority of the TGF-β pathway genes enhances HR efficiency. [siRNA screening database was used from Adamson et al., A genome-wide homologous recombination screen identifies the RNA-binding protein RBMX as a component of the DNA-damage response. *Nature Cell Biology*, 14: 318-328 (2012)]. Error bars represent mean±s.e.m.

FIG. 6A is a schematic showing that wild-type or Fancd2-deficient mice were exposed to the physiologic stress, pIpC. Mice were pretreated in vivo with either no Tgfβ inhibitor, the neutralizing antibody to Tgfβ 1, 2, 3, or the Tgfβ receptor kinase inhibitor, Galunisertib. Long-term HSCs (LT-HSCs) were isolated and subjected to functional tests.

FIG. 6B is a graph showing that the neutralizing antibody to Tgfβ 1, 2, 3 or the kinase inhibitor rescued the pIpC-induced DNA damage in the LT-HSCs as measured by the comet assay.

FIG. 6C is a graph showing that the neutralizing antibody to Tgfβ 1, 2, 3 or the kinase inhibitor rescued the pIpC-induced DNA damage, as measured by gamma H2AX foci.

DETAILED DESCRIPTION OF THE INVENTION

Figure 1:
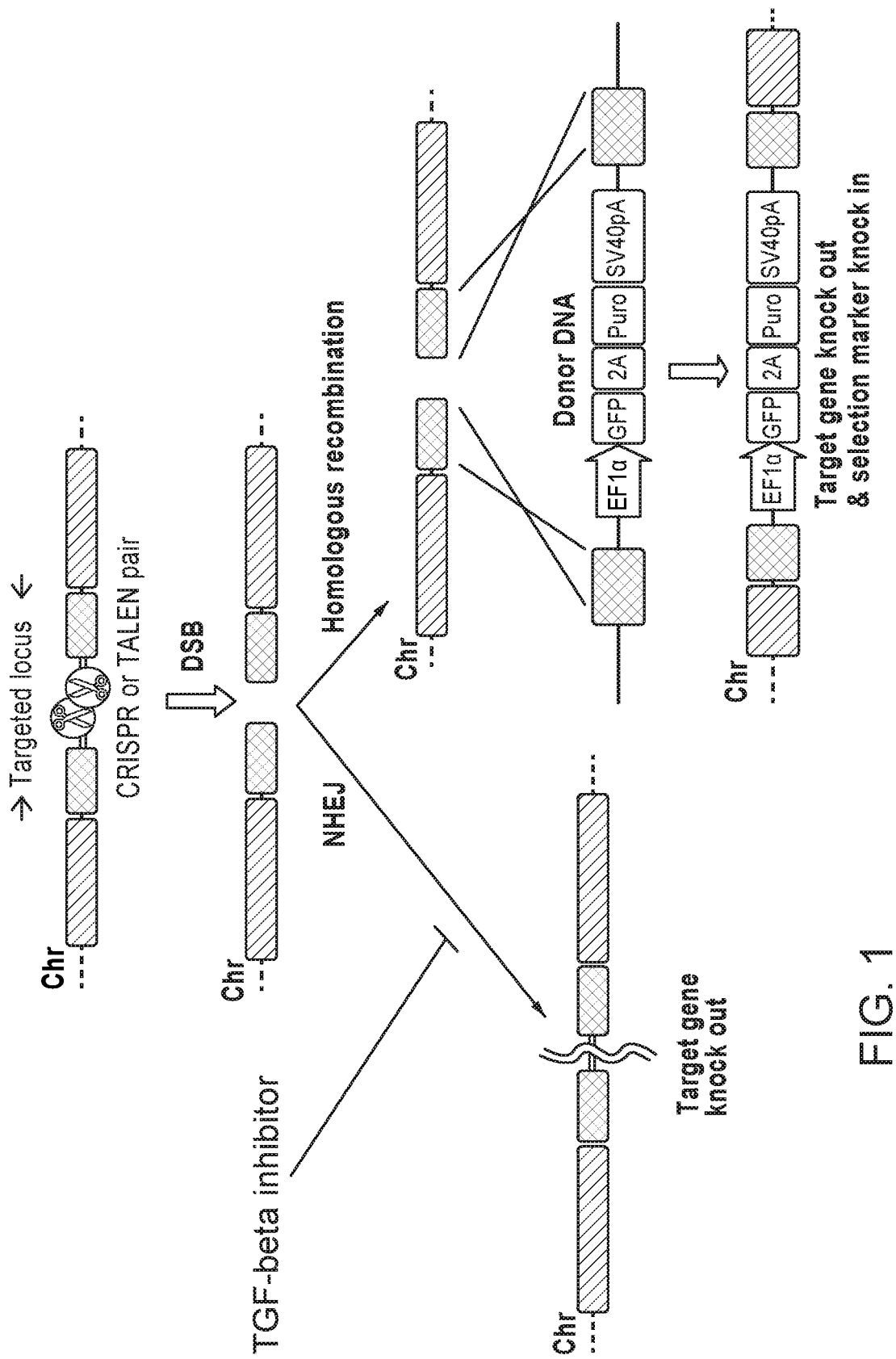
FIG. 1 is a schematic of the methods according to some embodiments of the invention.

The invention is based in part upon the surprising discovery that inhibition of the TGF-β pathway shifts the balance between non-homologous end joining (NHEJ) and homologous recombination (HR) DNA repair mechanisms in favor of HR. This shift results in more efficient DNA repair. Accordingly, the invention features methods of enhancing DNA repair during genome editing, such as genome editing using targeted nucleases.

Genome editing, or genome editing with engineered nucleases (GEEK) is a type of genetic engineering in which DNA is inserted, deleted or replaced in the genome of an organism using engineered nucleases, or "molecular scissors." There are currently four families of engineered nucleases being used for gene editing: Meganucleases, Zinc finger nucleases (ZFNs), Transcription Activator-Like Effector-based Nucleases (TALEN), and the CRISPR-Cas system. These nucleases create site-specific double-strand breaks (DSBs) at desired locations in the genome. The induced double-strand breaks are repaired through nonhomologous end-joining (NHEJ) or homologous recombination (HR), resulting in targeted mutations ('edits').

Successful use of nucleases in genome editing requires an understanding of DNA double stranded break (DSB) repair mechanisms. Two of the known DSB repair pathways that are essentially functional in all organisms are the non-homologous end joining (NHEJ) and homologous recombination (HR).

NHEJ uses a variety of enzymes to directly join the DNA ends in a double-strand break. In contrast, in HR, a homologous sequence is utilized as a template for regeneration of missing DNA sequence at the break point. The natural properties of these pathways form the very basis of nucleases based genome editing.

NHEJ is error-prone, and has been shown to cause mutations at the repair site in approximately 50% of DSB in mycobacteria, and also its low fidelity has been linked to mutational accumulation in leukemias. Thus if one is able to create a DSB at a desired gene in multiple samples, it is very likely that mutations will be generated at that site in some of the treatments because of errors created by the NHEJ infidelity.

On the other hand, the dependency of HR on a homologous sequence to repair DSBs can be exploited by inserting a desired sequence within a sequence that is homologous to the flanking sequences of a DSB which, when used as a template by FIR system, would lead to the creation of the desired change within the genomic region of interest.

The efficiency of NHEJ and HR mediated DSB repair varies substantially by cell type and cell state; in most cases, however, NHEJ is more active than HR. This difference in activity makes it more challenging to treat diseases that require gene correction or gene insertion than those requiring gene inactivation. NHEJ is thought to be active throughout the cell cycle and has been observed in a variety of cell types, including dividing and post-mitotic cells. NHEJ may therefore be used to facilitate high levels of gene disruption in target cell populations. In contrast, HDR acts primarily during the S/G2 phase and is therefore largely restricted to cells that are actively dividing, limiting treatments that require precise genome modifications to mitotic cells.

Recent advances in genome sequencing techniques and analysis methods have significantly accelerated the ability to catalog and map genetic factors associated with a diverse range of biological functions and diseases. Thus, precise genome targeting technologies such as genome editing will enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, in order for it to be a successful therapy the specificity and efficiency of the DSB repair by HR needs to be optimized.

The efficiency of correction by HR may be controlled by a number of factors. Suppressing competing DNA repair pathways such as NHEJ has been shown to increase HDR rates moderately. The present invention provides a safe and effective method for shifting a repair of a targeted DNA double-standed break towards the desired outcome, repair by homologous recombination. Specifically, the invention provides methods of increasing the efficiency of the repair of a targeted DNA-double stranded breaks by administering to a subject or contacting a cell with a TGF-β inhibitor. By "increase in efficiency" it is meant at least 5%, 10%, 15%, 20%, 25%, 50%, 100%, 200% or more efficient on the repair by homologous recombination in the presence of the TGF-β inhibitor compared to the absence of the TGF-β inhibitor. Alternatively, the phrase "increase in efficiency" refers to at least 2, 3, 4, 5, 6, 7, 8, 9, 10 fold more efficient on the repair by homologous recombination in the presence of the TGF-β inhibitor compared to the absence of the TGF-β inhibitor.

Targeted DNA-double stranded break may be introduced by any method known in the art, for example by AAV-mediate gene targeting or by programmable nuclease gene editing such as meganucleases, zinc finger nucleases, transcription activator like effector nucleases and the clustered regularly interspaced short palindromic repeat (CRISPR)-associated nuclease Cas9.

The cell is any cell in which a targeted DNA-double stranded break occurs. For example, the cell is a differentiated cell. In other embodiments, the cell is a primary cell.

The cell is for example, a liver cell, a kidney cell, a breast cell, a skin cell, a neuronal cell, a brain cell, a blood cell or a lung cell.

A TGFβ inhibitor is a compound that decreases expression or activity of TGFβ. A decrease in TGFβ activity is defined by a reduction of a biological function of TGFβ inhibitor. A TGFβ inhibitor can neutralize TGFβ, interfere with binding of TGFβ to its receptor or inhibits a component of the TGFβ signaling pathway such as SMAD3, MEK or pERK1/2.

The TGFβ inhibitor can be a small molecule, A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 115 kD, less than about 1 kD, less than 750 daltons, less than 500 daltons, less than about 450 daltons, less than about 400 daltons, less than about 350 daltons, less than 300 daltons, less than 250 daltons, less than about 200 daltons, less than about 150 daltons, less than about 100 daltons. Small molecules can be, e.g., nucleic acids, peptides, polypeptides, peptidomimetics, carbohydrates, lipids or other organic or inorganic molecules. For example, the small molecule IGFP inhibitor is a DNA dependent protein kinase inhibitor, a SMAD3 inhibitor, a 15-PGDH inhibitor, a TGFβR1 inhibitor, an AT1 antagonist or a MEK1/2 inhibitor.

A DNA dependent protein kinase inhibitor includes for Example, Compound 401, DMNB, KU 0060648, NU 7026, NU 7441, or PI 103 hydrochloride.

A SMAD3 inhibitor includes for example SIS3 or naringenin.

A 15-PGDH inhibitor includes for example SW033291.

A TGFβR1 inhibitor includes for example, Galunisertib, YR-290, SB431542, SB525334, SD208, LY2109761, SB505124, GW788388, LY364947, RepSox, or EW-7197. In some embodiments, the TGFβR1 inhibitor is Galunisertib.

An AT1 antagonist is for example losartan.

A MEK1/2 inhibitor includes for example, U0126, PD98059, PD0325901, PD184352, PD318088, SL327, AZD8330, U0126-EtOH, Trametinib, Pimasertib, or Binimetinib.

The compounds described above are summarized in Table 1 with corresponding chemical names.

TABLE 1

| Compound | Chemical Name |
| --- | --- |
| Compound 401 | 2-(4-Morpholinyl)-4H-pyrimido[2,1-a]isoquinolin-4-one |
| DMNB | 4,5-Dimethoxy-2-nitrobenzaldehyde |
| KU 0060648 | 4-Ethyl-N-[4-[2-(4-morpholinyl)-4-oxo-4H-1-benzopyran-8-yl]-1-dibenzothienyl]-1-piperazineacetamide |
| NU 7026 | 2-(4-Morpholinyl)-4H-naphthol[1,2-b]pyran-4-one |
| NU 7441 | 8-(4-Dibenzothienyl)-2-(4-morpholinyl)-4H-1-benzopyran-4-one |
| PI 103 hydrochloride | 3-[4-(4-Morpholinylpyrido[3',2':4,5]furo[3,2-d]pyrimidin-2-yl]phenol hydrochloride |
| SIS3 | 1-(3,4-dihydro-6,7-dimethoxy-2(1H)-isoquinolinyl)-3-(1-methyl-2-phenyl-1H-pyrrolo[2,3-b]pyridin-3-yl)-2-propen-1-one |
| Naringenin | 5,7-dihydroxy-2-(4-hydroxyphenyl)chroman-4-one |
| SW033291 | 2-(butylsulfinyl)-4-phenyl-6-(thiophen-2-yl)thieno[2,3-b]pyridin-3-amine |
| Galunisertib | 4-[2-(6-methylpyridin-2-yl)-5,6-dihydro-4H-pyrrolo[1,2-b]pyrazol-3-yl]quinoline-6-carboxamide |
| YR-290 | N-phenylacetyl-1,3,4,9-tetrahydro-1H-beta-carboline |
| SB431542 | 4-[4-(1,3-benzodioxol-5-yl)-5-pyridin-2-yl-1H-imidazol-2-yl]benzamide |
| SB525334 | 6-[2-(1,1-Dimethylethyl)-5-(6-methyl-2-pyridinyl)-1H-imidazol-4-yl]quinoxaline |
| SD208 | 2-(5-Chloro-2-fluorophenyl)-4-[(4-pyridyl)amino]pteridine |
| LY2109761 | 4-[2-[4-(2-pyridin-2-yl-5,6-dihydro-4H-pyrrolo[1,2-b]pyrazol-3-yl)quinolin-7-yl]oxyethyl]morpholine |
| SB505124 | 2-[4-(1,3-Benzodioxol-5-yl)-2-(1,1-dimethylethyl)-1H-imidazol-5-yl]-6-methyl-pyridine |
| GW788388 | N-(oxan-4-yl)-4-[4-(5-pyridin-2-yl-1H-pyrazol-4-yl)pyridin-2-yl]benzamide |
| LY364947 | 4-[3-(2-pyridinyl)-1H-pyrazol-4-yl]-quinoline |
| RepSox | 2-[5-(6-methylpyridin-2-yl)-1H-pyrazol-4-yl]-1,5-naphthyridine |
| EW-7197 | N-((4-([1,2,4]triazolo[1,5-a]pyridin-6-yl)-5-(6-methylpyridin-2-yl)-1H-imidazol-2-yl)methyl)-2-fluoroaniline |
| losartan | [2-butyl-5-chloro-3-[[4-[2-(2H-tetrazol-5-yl)phenyl]phenyl]methyl]imidazol-4-yl]methanol |
| U0126 | (2Z,3Z)-2,3-bis[amino-(2-aminophenyl)sulfanylmethylidene]butanedinitrile |
| U0126-EtOH | (2Z,3Z)-2,3-bis[amino-(2-aminophenyl)sulfanylmethylidene]butanedinitrile; ethanol |
| PD98059 | 2'-amino-3'-methoxyflavone |
| PD0325901 | N-[(2R)-2,3-Dihydroxypropoxy]-3,4-difluoro-2-[(2-fluoro-4-iodophenyl)amino]-benzamide |
| PD184352 | 2-(2-Chloro-4-iodophenylamino)-N-cyclopropylmethoxy-3,4-difluorobenzamide |
| PD318088 | 5-bromo-N-(2,3-dihydroxypropoxy)-3,4-difluoro-2-(2-fluoro-4-iodoanilino)benzamide |
| SL327 | (Z)-3-amino-3-(4-aminophenyl)sulfanyl-2-[2-(trifluoromethyl)phenyl]prop-2-enenitrile |
| AZD8330 | 2-(2-fluoro-4-iodoanilino)-N-(2-hydroxyethoxy)-1,5-dimethyl-6-oxopyridine-3-carboxamide |
| Trametinib | N-[3-[3-cyclopropyl-5-(2-fluoro-4-iodoanilino)-6,8-dimethyl-2,4,7-trioxopyrido[4,3-d]pyrimidin-1-yl]phenyl]acetamide |
| Pimasertib | N-[(2S)-2,3-dihydroxypropyl]-3-(2-fluoro-4-iodoanilino)pyridine-4-carboxamide |
| Binimetinib | 6-(4-bromo-2-fluoroanilino)-7-fluoro-N-(2-hydroxyethoxy)-3-methylbenzimidazole-5-carboxamide |

The TGFβ inhibitor is an antibody or fragment thereof specific to TGFβ or TGFβR1. Methods for designing and producing specific antibodies are well-known in the art.

The TGFβ inhibitor is for example an antisense TGFβ nucleic acid, a TGFβ-specific short-interfering RNA, or a TGFβ-specific ribozyme. Alternatively, the TGFβ inhibitor is for example an antisense SMAD3 nucleic acid, a SMAD3-specific short-interfering RNA, or a SMAD3-specific ribozyme. By the term "siRNA" is meant a double stranded RNA molecule which prevents translation of a target mRNA. Standard techniques of introducing siRNA into a cell are used, including those in which DNA is a template from which an siRNA is transcribed. The siRNA includes a sense TGFβ or SMAD3 nucleic acid sequence, an anti-sense TGFβ or SMAD3 nucleic acid sequence or both. Optionally, the siRNA is constructed such that a single transcript has both the sense and cotnplementary antisense sequences from the target gene, e.g., a hairpin (shRNA). Optionally, the siRNA is constructed as a short guided RNA (sgRNA). Examples of siRNAs shRNAs and sgRNA are disclosed in the examples herein.

Binding of the siRNA to a TGFβ or SMAD3transcript in the target cell results in a reduction in TGFβ or SMAD3 production by the cell. The length of the oligonucleotide is at least 10 nucleotides and may be as long as the naturally-occurring TGFβ or SMAD3 transcript. Preferably, the oligonucleotide is 19-25 nucleotides in length. Most preferably, the oligonucleotide is less than 75, 50, 25 nucleotides in length.

The TGFβ inhibitor is administered locally, directly to the cell or systemically. The TGFβ inhibitor is administered before, during or after the cell undergoes genome editing. The TGFβ inhibitor is at least 1, 2, 3, 4, 5 or more days before the genome editing. The TGFβ inhibitor is at least 1, 2, 3, 4, 5, 6, 7, 8, 9, 10, 15, 20, 25, 30 or more days after the genome editing. The TCFβ inhibitor is at least 1, 2, 3, 4, 5, 6, or more months after the genome editing.

In further embodiments, the TGFβ inhibitor is administered in combination with a KU170 inhibitor or a DNA ligase IV inhibitor. The KU70 inhibitor or a DNA ligase IV inhibitor is administered concurrently with the TGFβ inhibitor, before the TGFβ inhibitor or after the TGFβ inhibitor.

Definitions

The term "TGFβ" or "transforming growth factor-beta" refers to the family of molecules described that have either the full-length, native amino acid sequence of any of the humans TGFβ isoforms.

A "TGFβ antibody" refers to an antibody or antigen binding fragment thereof that binds to any of the isoforms of TGFβ, preferably binding to either TGFβ1, TGFβ2, or TGFβ3, or to any combination thereof.

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073, incorporated by reference herein in its entirety.

Zinc finger binding domains can be "engineered" to bind to a predetermined nucleotide sequence, for example via engineering (altering one or more amino acids) of the recognition helix region of a naturally occurring zinc finger protein. Similarly, TALEs can be "engineered" to bind to a predetermined nucleotide sequence, for example by engineering of the amino acids involved in DNA binding (the RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925, 523; 6,007,988; 6,013,453; 6,200,759; WO 95/19431; WO 96/06166; WO 98/53057; WO 98/54311; WO 00/27878; WO 01/60970 WO 01/88197 and WO 02/099084.

As used herein, the term "Cas protein" refers to an essential protein component in the CRISPR/Cas system, forms an active endonuclease or nickase when complexed with two RNAs termed CRISPR RNA (crRNA) and trans-activating crRNA (tracrRNA).

The information on the gene and protein of Cas are available from GenBank of National Center for Biotechnology Information (NCBI), without limitation.

The CRISPR-associated (cas) genes encoding Cas proteins are often associated with CRISPR repeat-spacer arrays. More than forty different Cas protein families have been described. Of these protein families, Cas1 appears to be ubiquitous among different CRISPR/Cas systems. There are three types of CRISPR-Cas system. Among them, Type II CRISPR/Cas system involving Cas9 protein and crRNA and tracrRNA is representative and is well known. Particular combinations of cas genes and repeat structures have been used to define 8 CRISPR subtypes (Ecoli, Ypest, Nmeni, Dvulg, Tneap, Hmari, Apern, and Mtube).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that farms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/006414174, 2007/0218528; 2008/0131962 and 20110201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the teen "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See, Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCI WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolatereductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

EXAMPLES

Example 1

Figure 2A:
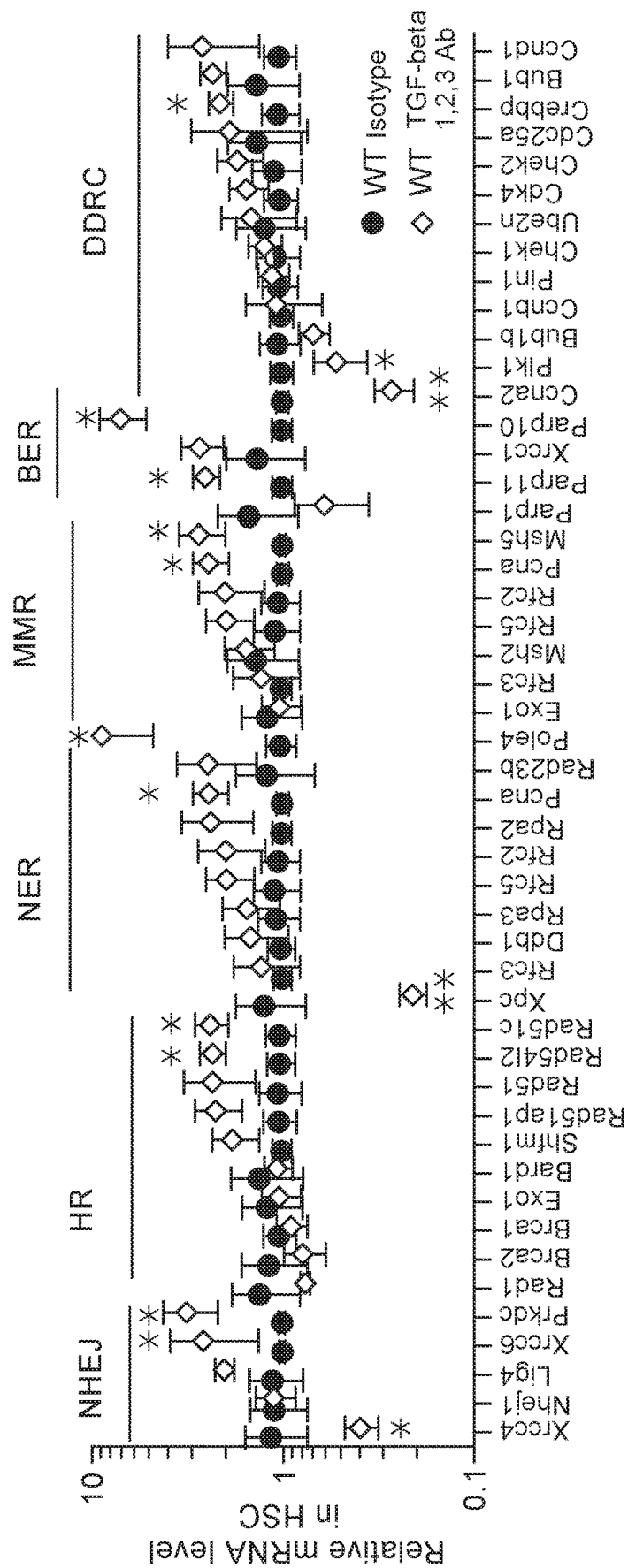
FIGS. 2A-2H are graphs showing that TGF-β pathway inhibition upregulates HR and downregulates NHEJ in HSCs from Fancd2−/− mice FA.
Figure 2B:
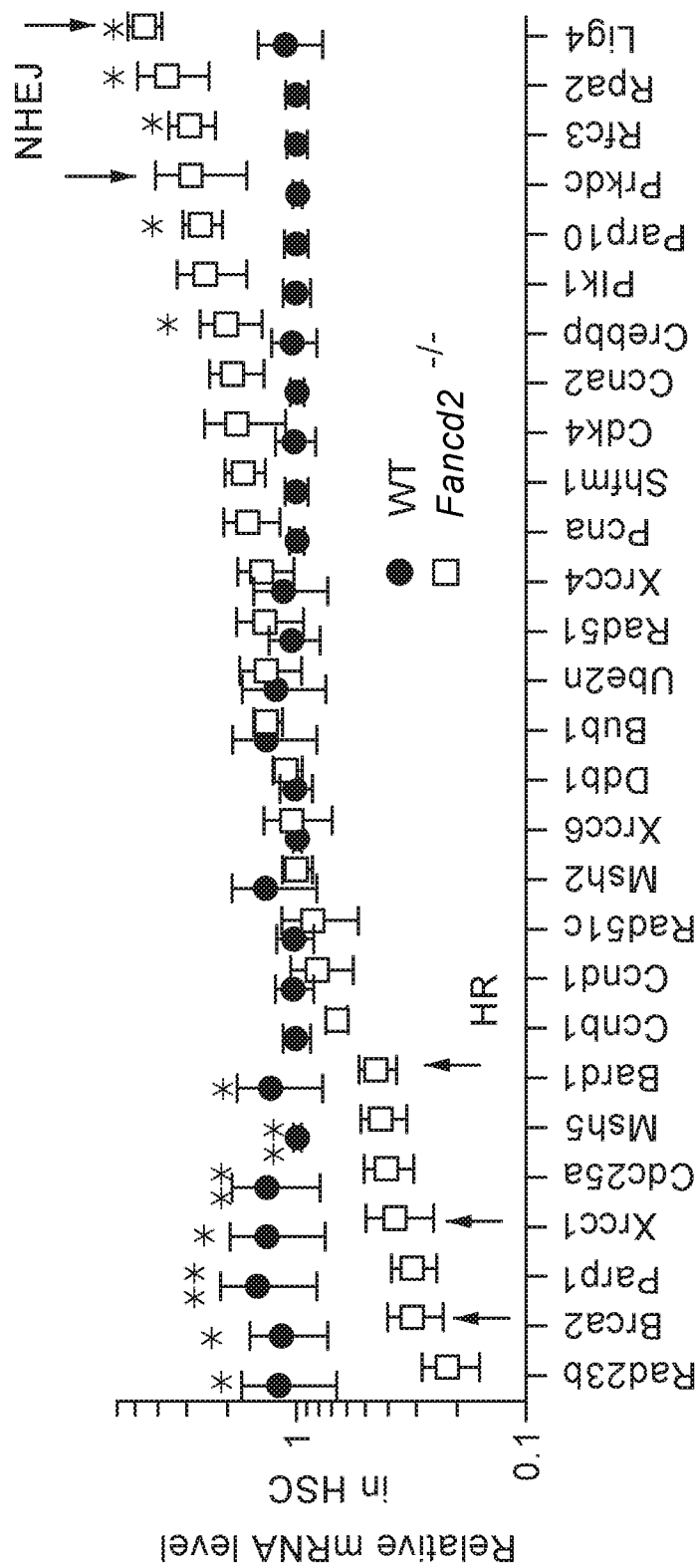
Figure 2C:
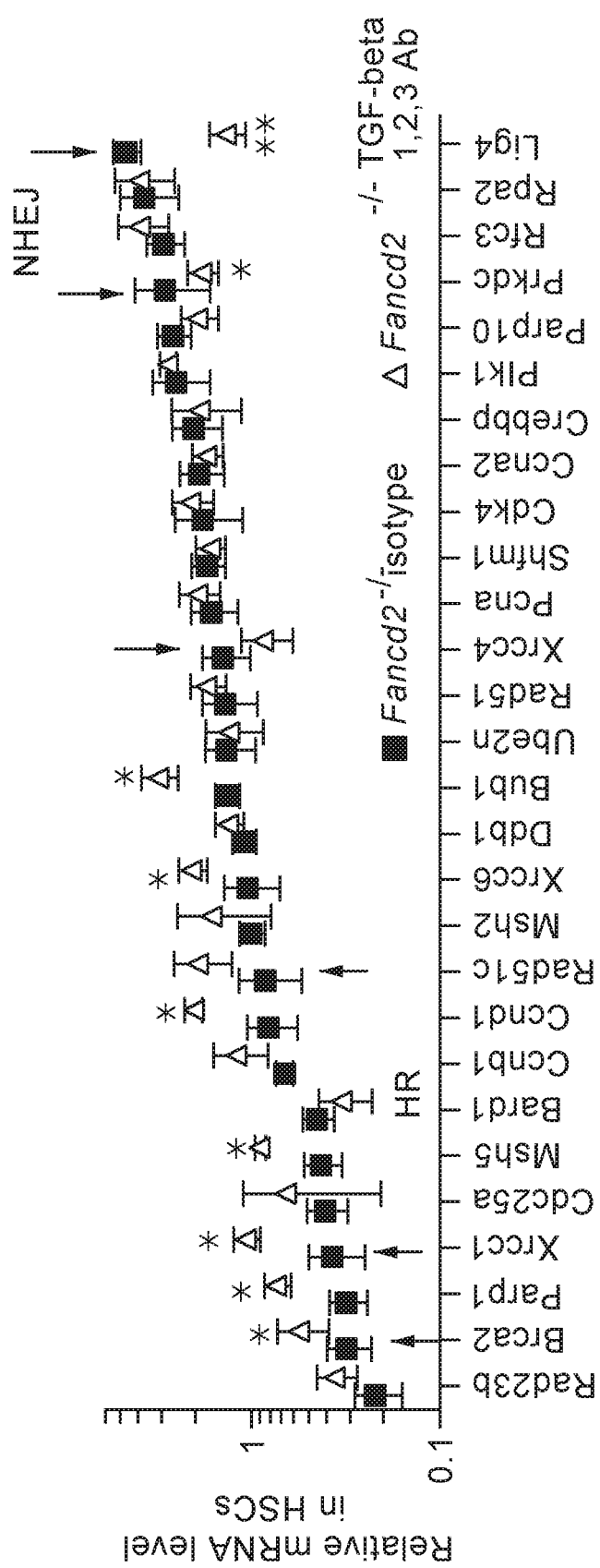
Figure 2D:
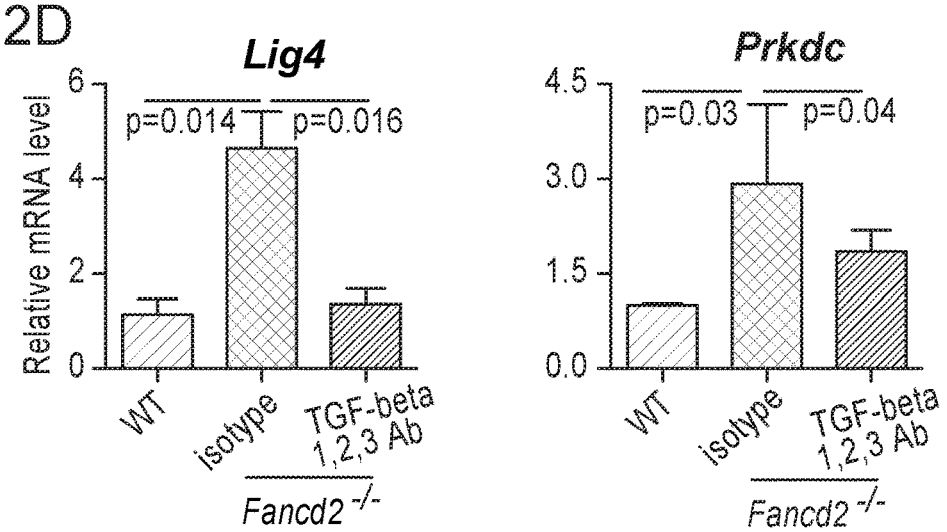
Figure 2E:
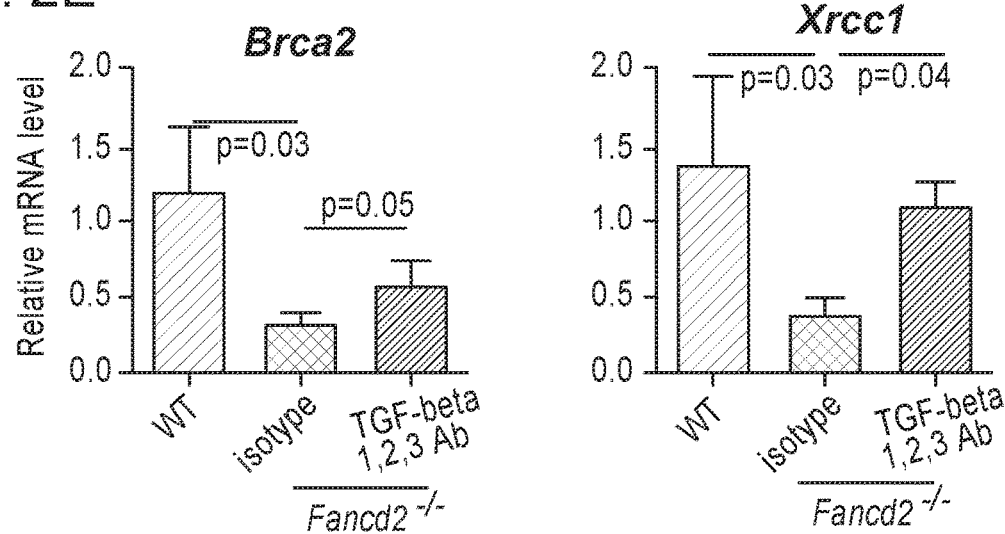
Figure 2F:
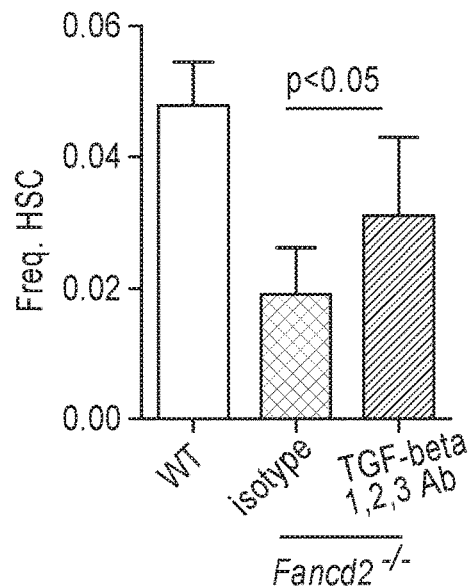
Figure 2G:
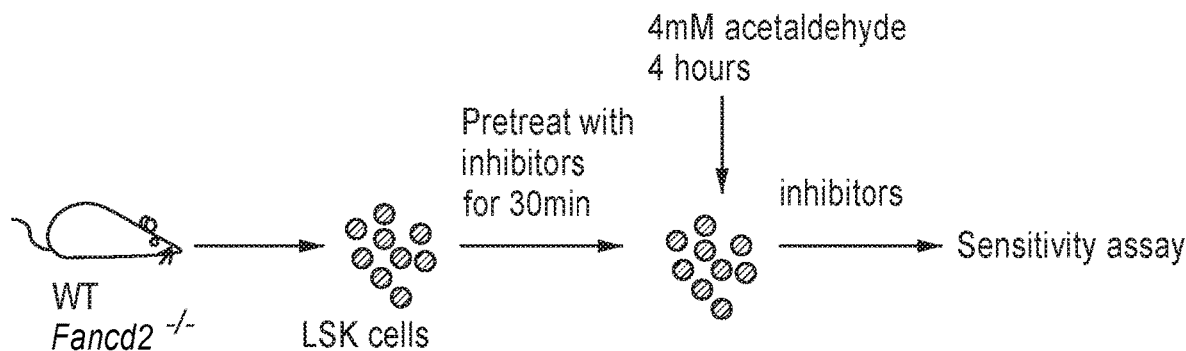
Figure 2H:
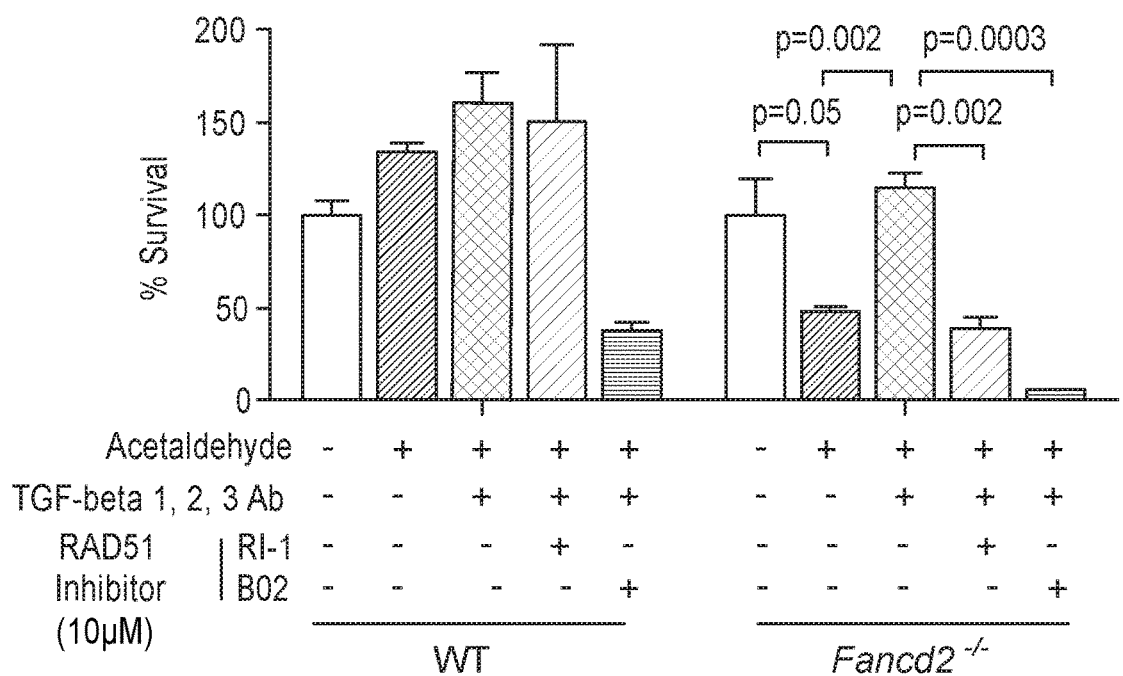
Figure 3A:
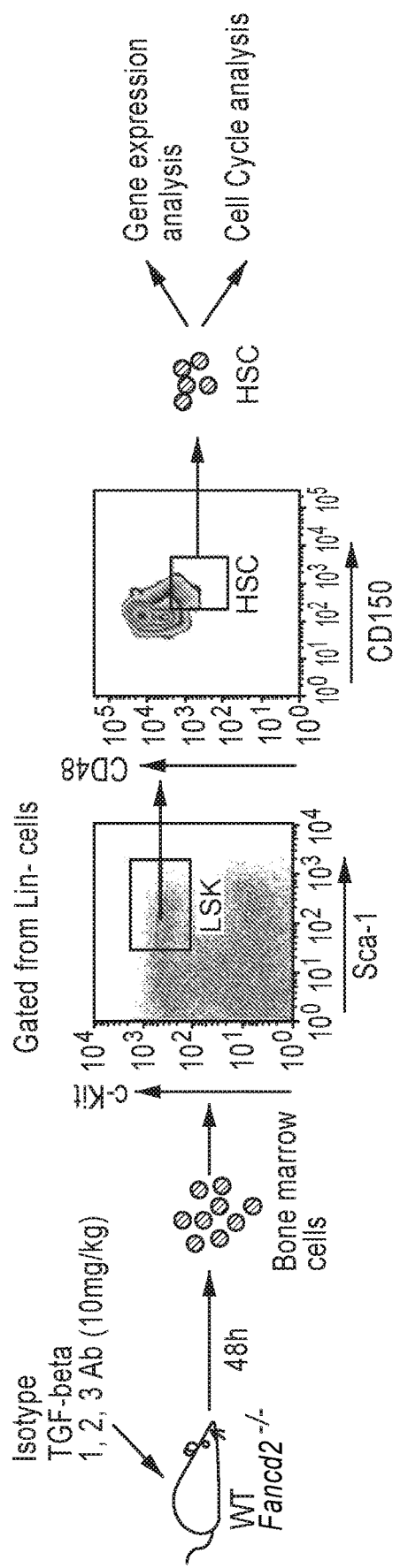
FIGS. 3A-3H are graphs showing that inhibition of TGF-β pathway in murine HSPCs promotes DNA repair activity.
Figure 3B:
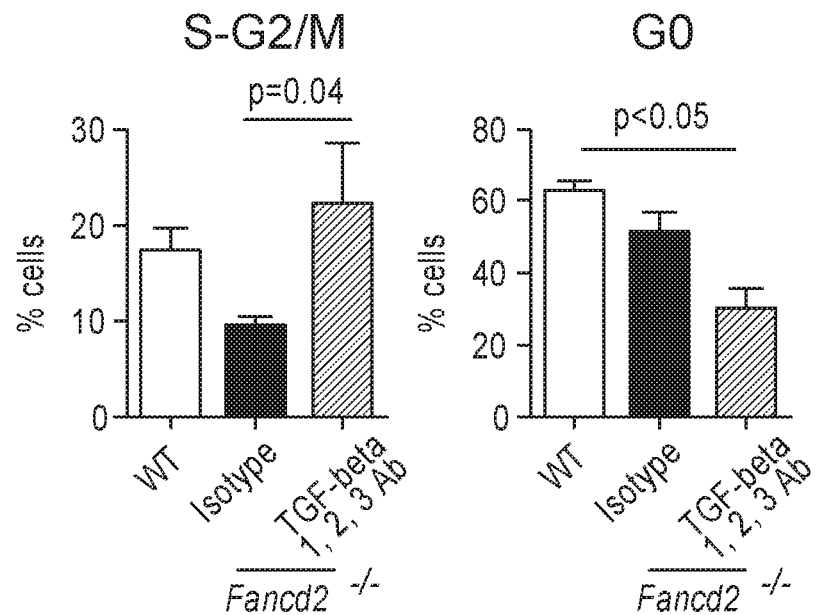
Figure 3C:
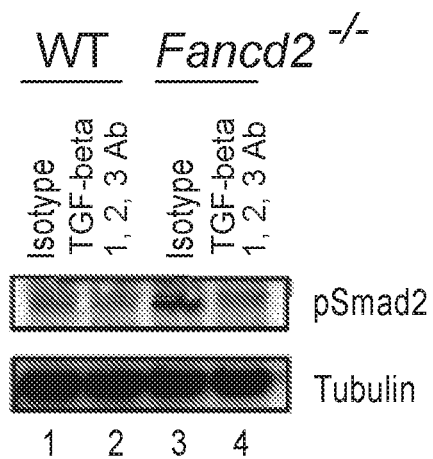
Figure 3D:
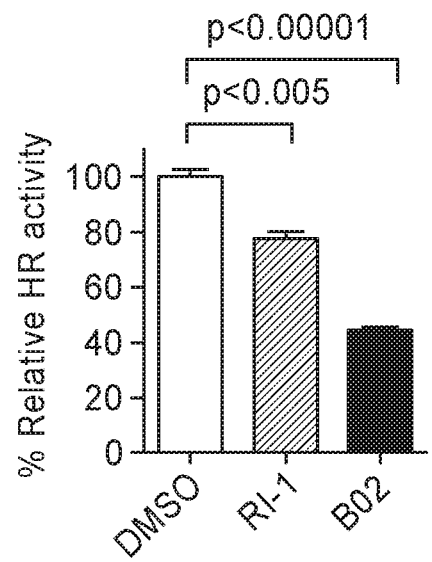
Figure 3E:
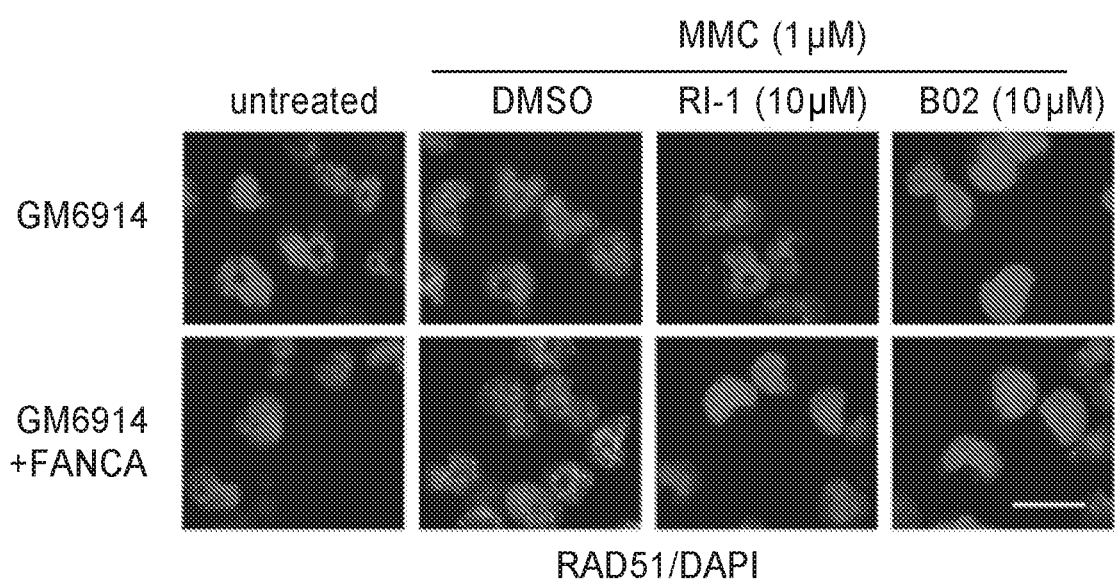
Figure 3F:
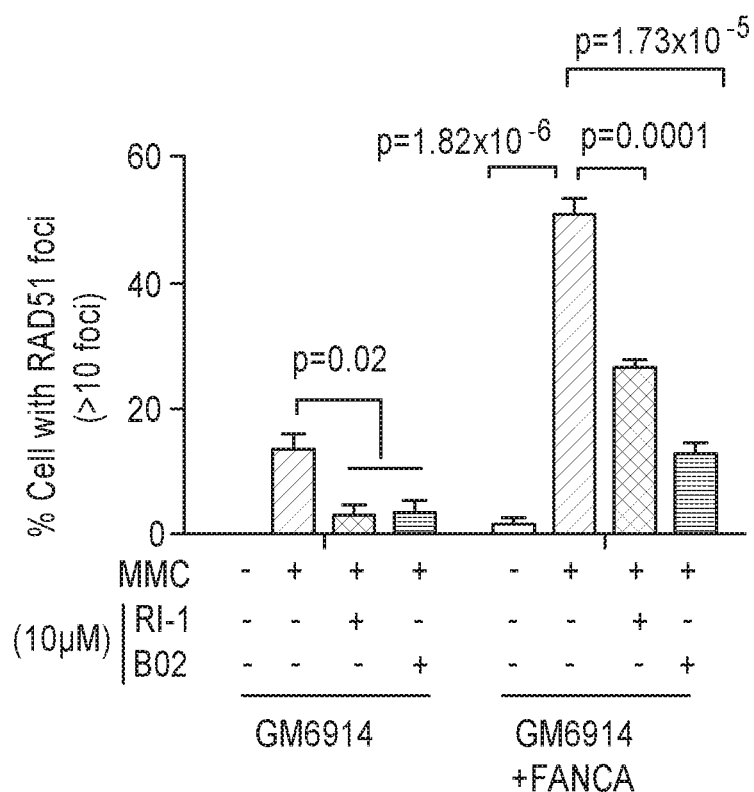
Figure 3G:
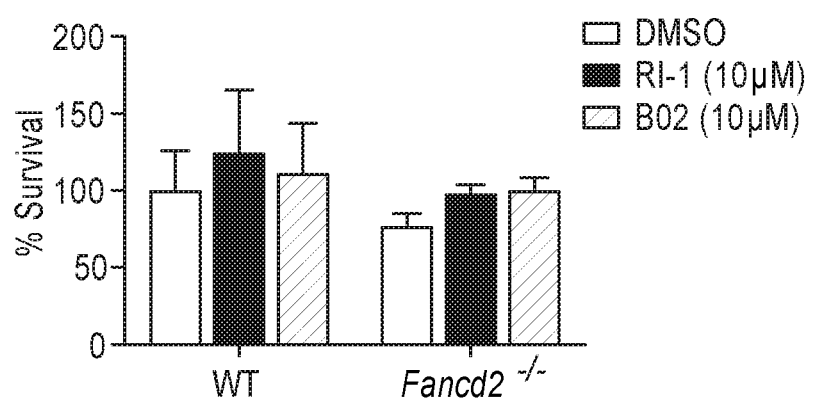
Figure 3H:
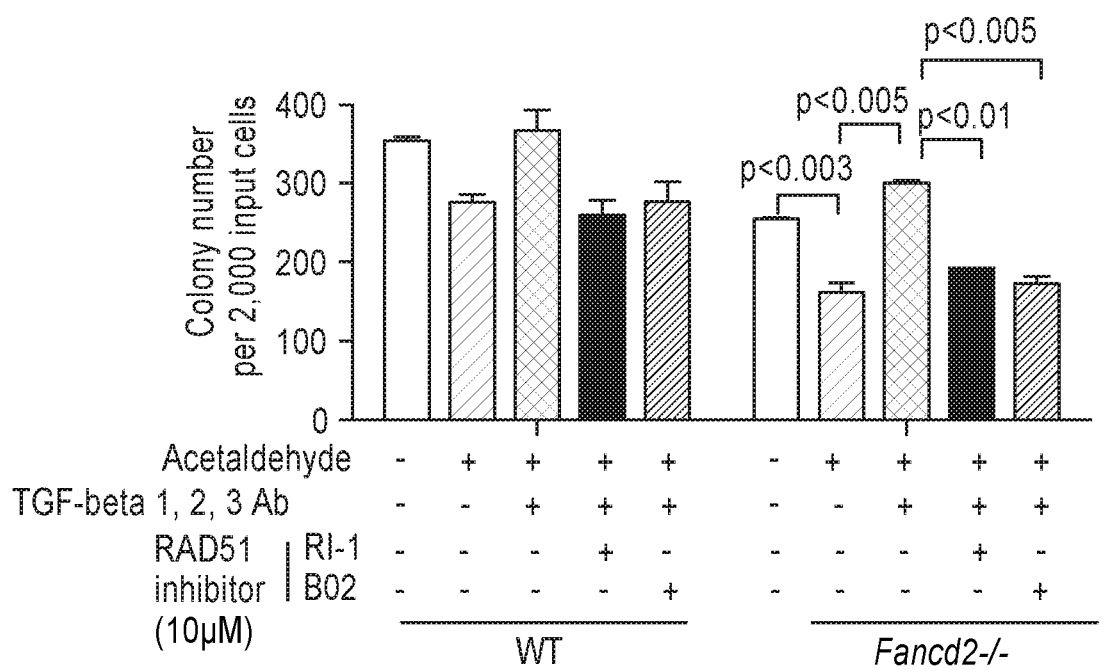
Figure 6A:
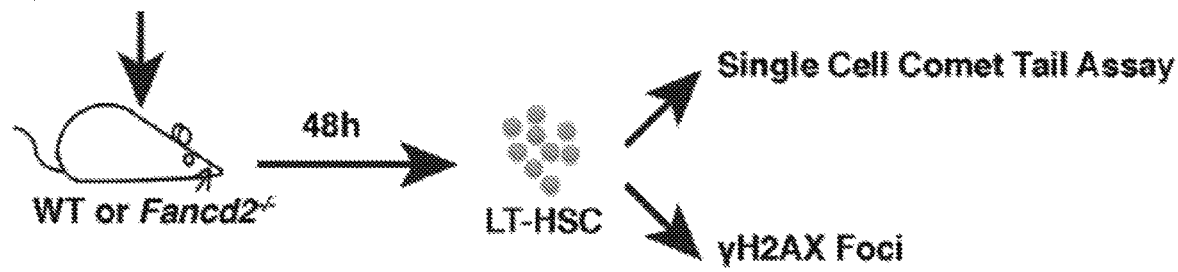
FIGS. 6A-6C are graphs showing that inhibition of TGFβ signaling with a small molecule kinase inhibitor (Galunisertib, LY2157299) rescues physiological stress-induced bone marrow failure in mice.
Figure 6B:
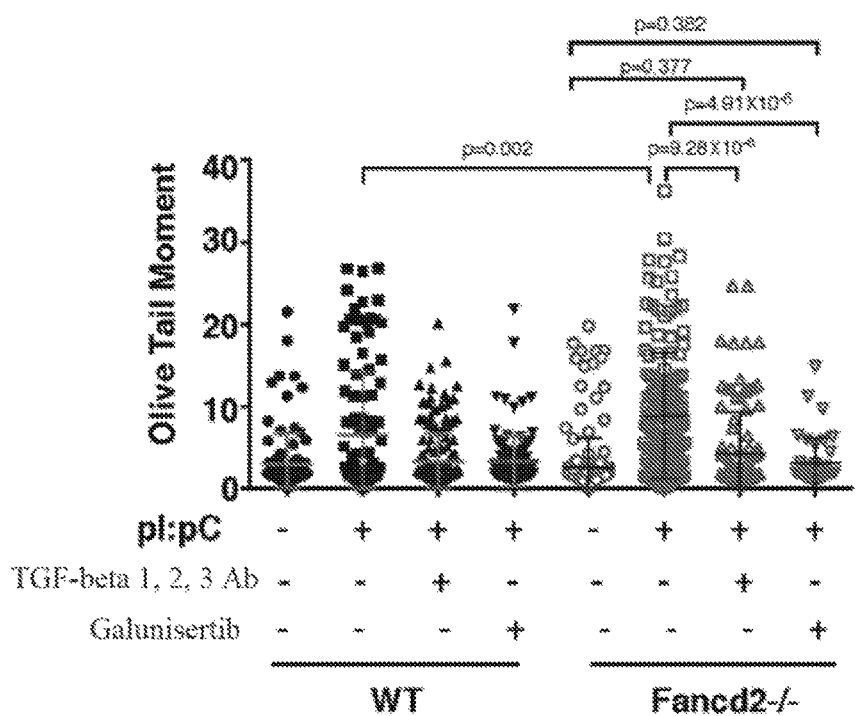
Figure 6C:
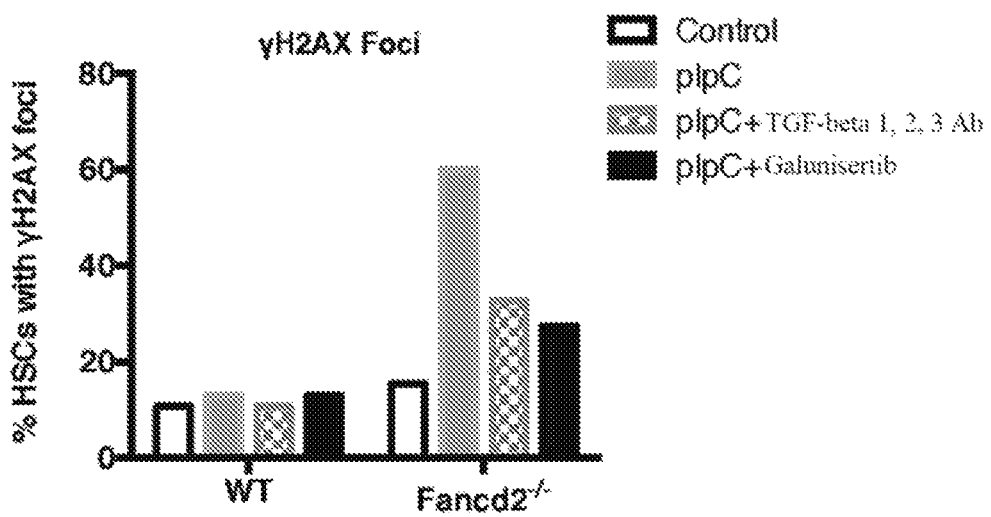
Figure 7:
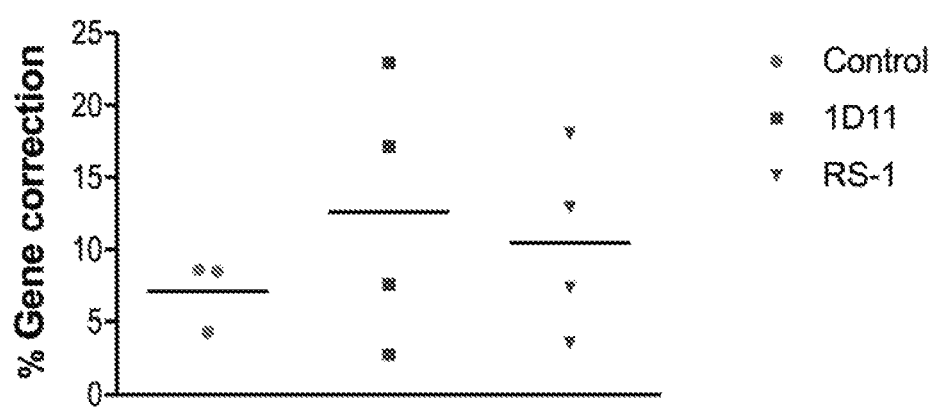
FIG. 7 is a graph showing hepatocyte gene correction efficiency in neonates.

TGF-β Pathway Inhibition Upregulates HR And Downregulates NHEJ in HSCs of FA Mice To determine the molecular mechanism by which TGF-β pathway regulates DNA repair and rescues genotoxicity in HSCs, we analyzed the expression of DNA repair genes in HSCs. Genes associated with NHEJ, HR, nucleotide excision repair (NER), mismatch repair (MMR), and the DNA damage response (DDR) were evaluated. Interestingly, over 70% of DNA repair genes examined were significantly upregulated in HSCs from WT mice exposed to a neutralizing anti-murine TGF-β monoclonal antibody (FIGS. 2A and 3A). In contrast, many genes involved in NHEJ were upregulated and many genes involved in HR were down-regulated in HSCs from Fancb2−/− mice, when compared to WT HSCs (FIG. 2B). This skewed expression pattern in Fancd2−/− HSCs was reversed by TGF-β pathway inhibition, as inhibitor treatment induced expression of HR genes such as Brca2 and Xrcc1 in Fancd2−/− HSCs, and caused a concomitant reduction of NHEJ gene expression, such as Lig4 and Prkdc (FIGS. 2C-2E). Previous studies have shown that FIR is upregulated when HSCs are driven into the cell cycle, thereby resulting in repair of double strand breaks (Beerman et al., 2014). Accordingly, the increase in HR activity in FA HSCs following TGF-β pathway inhibition may result, at least in part, from the release from cell cycle arrest (FIG. 3B), subsequently leading to a higher frequency of HSCs in FA mice (FIG. 2F). To confirm that inhibition of TGF-β pathway in HSCs creates an HR-competent state and thereby functionally protects them from genotoxicity, we inhibited both HR and TGF-β pathway and examined the survival of cells after acetaldehyde exposure (FIG. 2G). We used pharmacologic inhibitors which blocked HR, resulting in the reduction of RAD51 foci and the inhibition of DR-GFP plasmid recombination in a reporter assay (FIGS. 3D-3F). As expected, neutralizing anti-murine TGF-β monoclonal antibody exposure inhibited TGF-β pathway signaling in 14 bone marrow from FA mice (FIG. 6C). Interestingly, the anti-murine TGF-β monoclonal antibody did not protect the HSPCs from acetaldehyde-induced genotoxicity when HR was inhibited by pharmacologic inhibitors of PAD51 (Budke et al., 2012; Huang et al., 2012) (FIGS. 2H, 3G and 3H). Collectively, these data indicate that TGF-β pathway inhibition upregulates HR and downramlates NHEJ in HSPCs of Fancb2−/− mice and functionally promotes their survival.

Example 2

TGF-B Pathway Inhibition Increases HR and Decreases NHEJ in FA Cells

Figure 4A:
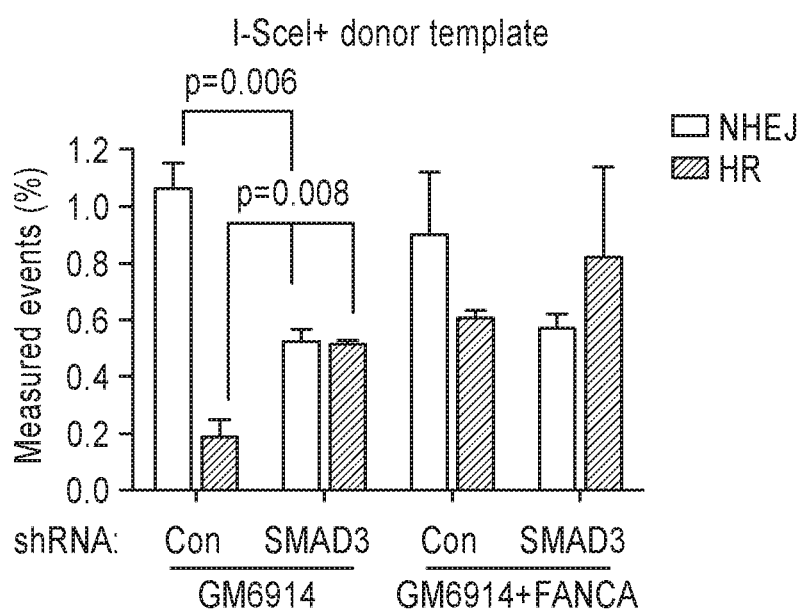
FIGS. 4A-4G are graphs showing that TGF-β pathway inhibition increases HR and decreases NHEJ activities in FA cells.
Figure 4B:
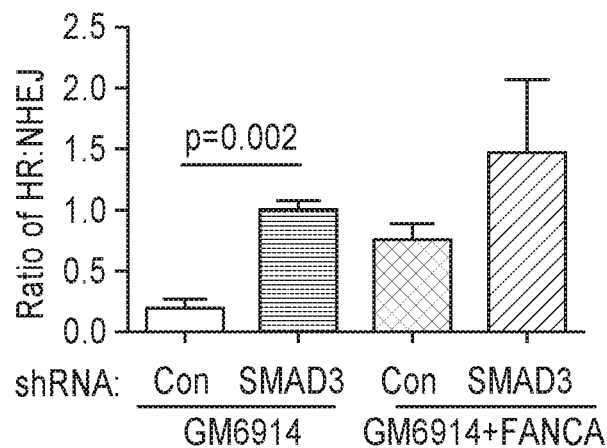
Figure 4C:
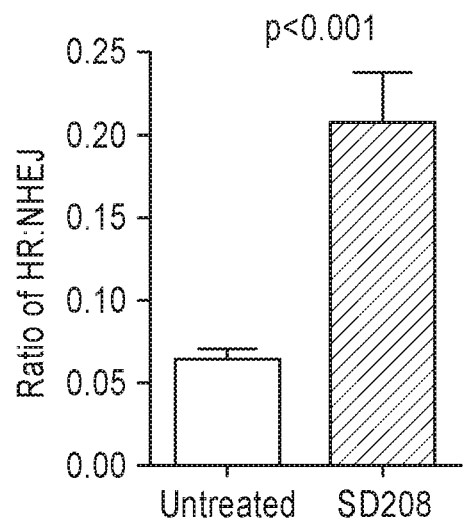
Figure 4D:
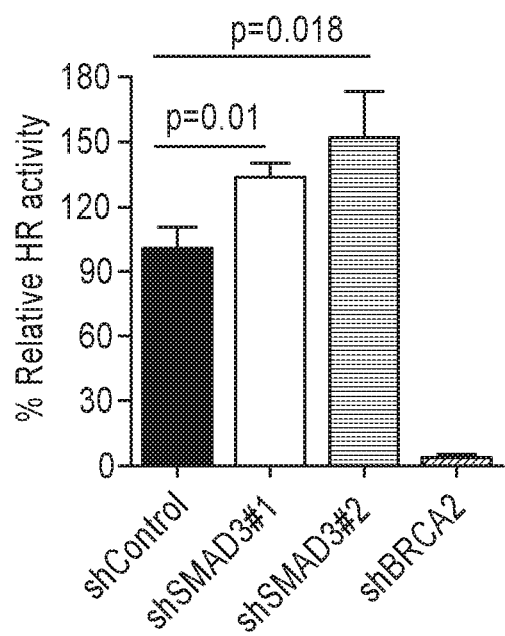
Figure 4E:
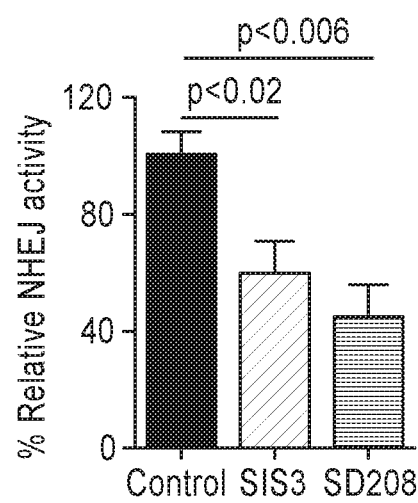
Figure 4F:
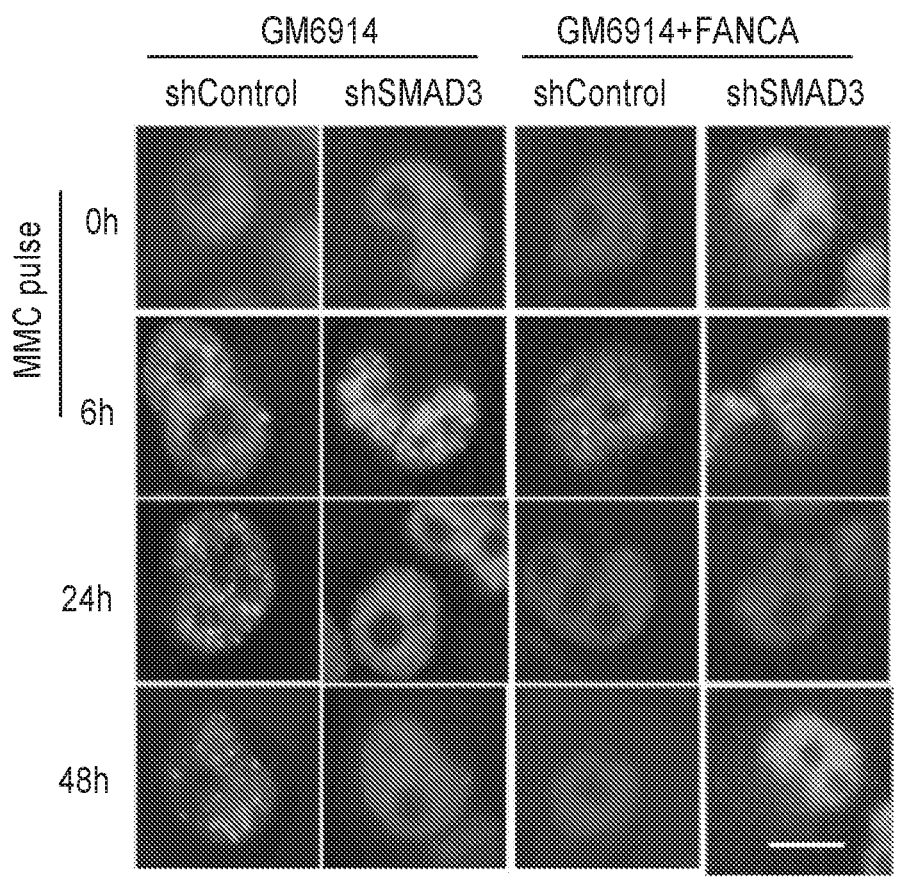
Figure 4G:
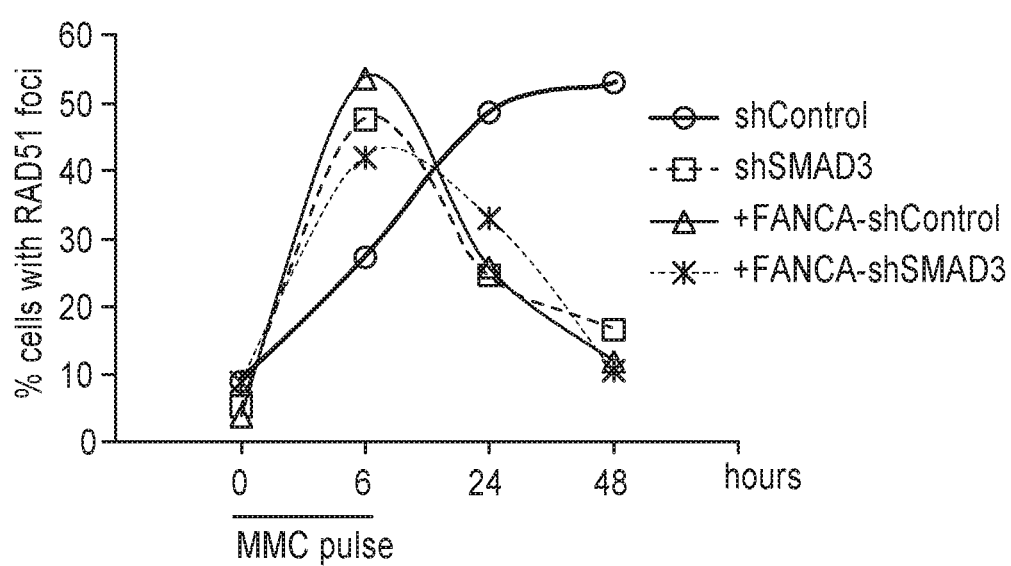
Figure 5A:
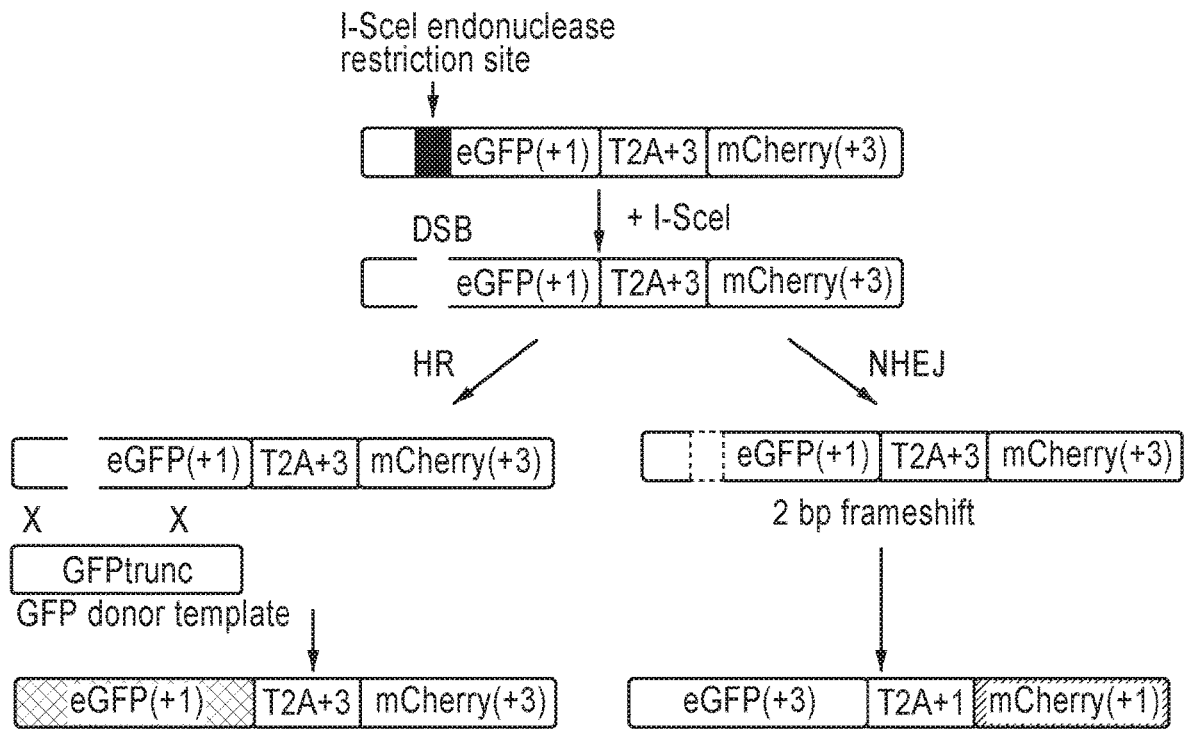
FIGS. 5A-5D are graphs showing that inhibition of TGF-β pathway increases HR activity and decreases NHEJ activity in FA cells.
Figure 5B:
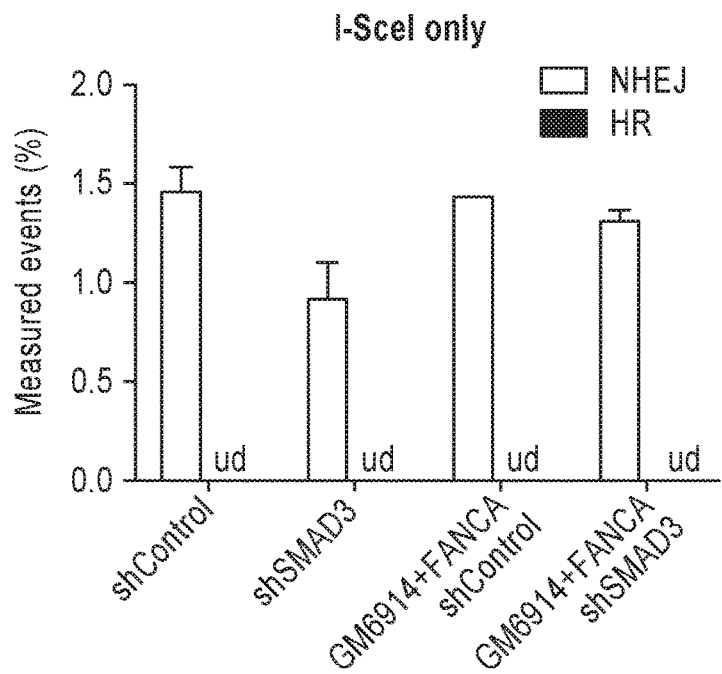
Figure 5C:
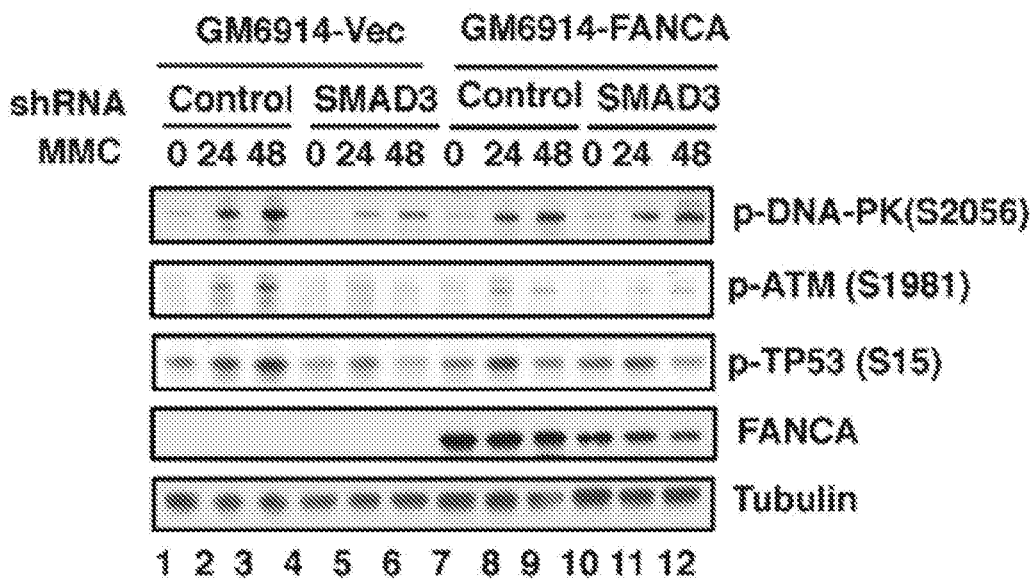
Figure 5D:
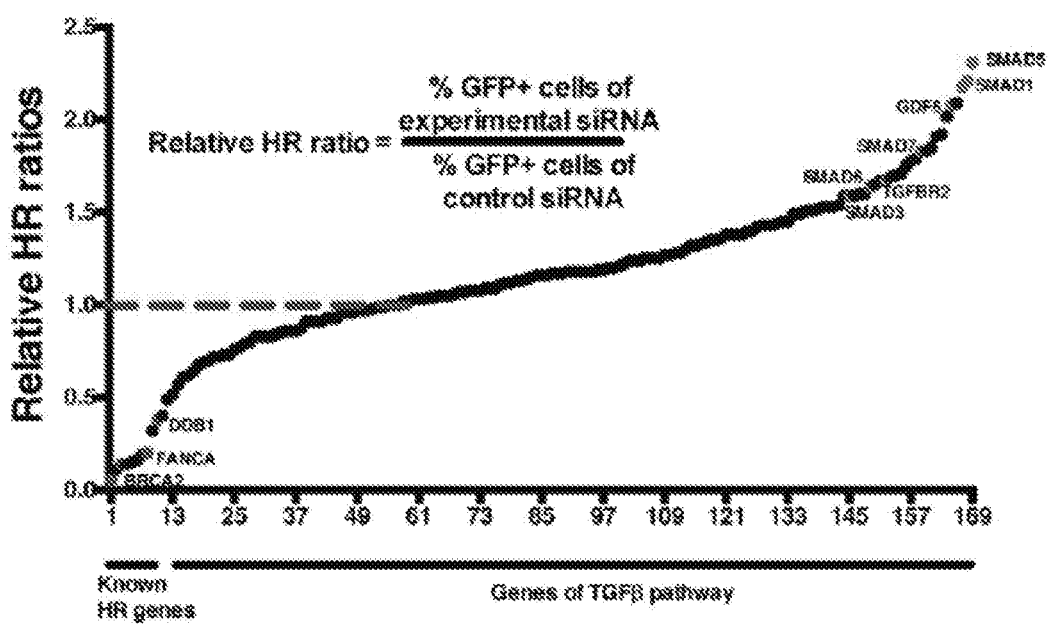

To directly confirm that inhibition of TGF-β pathway modulates HR or NHEJ activity, we engineered an individual DNA breakpoint in FA (GM6914) cells and employed the traffic light reporter (UR) system which quantifies both HR and NHEJ activities (Certo et al., 2011). In the TLR assay, double strand break (DSB) generated by 1-SceI endonuclease can be repaired by either HR or NHEJ pathway when the donor repair template is provided, however, the DSB can be repaired by NHEJ only when the repair template is missing (FIG. 5A). NHEJ and not HR activity was observed in FA cells when the donor repair template was missing (FIG. 5B), validating the assay. As predicted, FA (GM6914) cells exhibited fewer HR events compared to the FA-A-corrected (GM6914+FANCA) cells (FIG. 4A). Interestingly, TGF-β pathway inhibition, by knockdown of SMAD3, in FA cells resulted in increased HR events with a concomitant decrease in NHEJ events (FIGS. 4A and 4B). Inhibition of TGF-β pathway by the small molecule inhibitor SD208 also resulted in increased HR activity in FA cells (FIG. 4C). Similar findings were revealed when different reporter systems were used to quantify the HR and NHEJ activities individually (FIGS. 4D and 4E). Consistently, knockdown of SMAD3 in FA cells resulted in decreased phosphorylation of DNA-PK, a marker of NHEJ (FIG. 5C). Additionally, damage-induced RAD51 foci resolved more quickly in SMAD3-depleted FA cells 15 (FIGS. 4F and 4G), implying that HR-mediated DNA repair is more efficient in these cells. Analysis of the genome-wide siRNA screening data (Adamson et al., 2012) revealed that siRNA mediated knockdown of several TGF-β pathway genes enhanced FIR activity (FIG. 5D). Taken together, these data indicate that TGF-β pathway inhibition promotes DNA repair by directly increasing HR activity in FA cells.

Example 3

In Vitro Gene Targeting of Human Liver Cells

The goal of this example is to target and modify the human albumin gene locus in HepG2 cells using homologous recombination. We have developed an rAAV vector containing homology to the human albumin gene as well as a guide-strand RNA expression cassette designed to created a CRISPR/cas9 mediated double-strand break in the target region. The albumin sequence in the vector bears a single-base change designed to alter the endogenous albumin mRNA and protein. We have developed a second rAAV vector capable of expressing cas9 specifically in hepatic cells (liver specific promoter).

HepG2 cells will be co-transduced with both vectors at varying MOIs (multiplicity of infection) with and without concurrent inhibition of the TGF-beta pathway. Treated cells will be expanded and the albumin mRNA will be amplified and sequenced.

It is expected that some cells will express a modified albumin mRNA bearing the amino acid change contained within the donor rAAV sequence. TGF-beta inhibition will enhance the recombination frequency and hence yield higher levels of modified mRNA.

Example 4

In Vivo Gene Targeting of Hepatocytes

The goal of this example is to target and modify the human albumin gene locus in primary human hepatocytes in vivo using homologous recombination. This is a key proof-of-principle experiment in terms of in vivo liver gene targeting in humans.

We will use the same rAAV vectors described in the in vitro experiments above. Our routinely generated mice highly repopulated with human primary hepatocytes (mice with human livers). Highly chimeric (>90%) liver humanized mice will be injected with both rAAV vectors at a dose of $1 \times 10^{11}$ vg/mouse. This will be done both with and without concurrent TGF-beta inhibition. We will start mice on TGF-beta blocking drugs 2 days before vector injection and continue the treatment of another 10 days post injection. Controls will receive placebo.

Mice will be sacrificed 4 weeks after treatment and human albumin mRNA will be amplified and deeply sequenced, measuring the percentage of gene targeted cells in the population.

It is expected that TGF-beta inhibition will enhance the recombination frequency and hence yield higher levels of modified mRNA.

Example 5

In Vivo Gene Targeting of Mouse Hepatocytes

The goal of this example is to target and repair a disease causing mutation in mouse hepatocytes in situ vivo using homologous recombination.

We have already done this successfully and have validated the vectors to be used. The mouse disease model carries a point mutation in fumarylacetoacetate hydrolase (Fah). Deficiency of this enzyme causes hereditary tyrosinemia in humans.

We have 2 vectors: a) an rAAV containing the normal wild-type Fah genomic sequence and a guide-strand expression cassette; b) the cas9 expressing rAAV described above. Co-injection of these vectors into neonatal mice yields 15% gene repair. In adults, the efficiency is <1%. Mice will be injected with both rAAV vectors at a dose of $1 \times 10^{11}$ vg/mouse. This will be done both with and without concurrent TGF-beta inhibition. In adults we will start mice on TGF-beta blocking drugs 2 days before vector injection and continue the treatment of another 10 days post injection. Controls will receive placebo. In neonates, the TGF-beta inhibition will start at birth and continue for 2 weeks.

Mice will be sacrificed one month after treatment and the percentage of gene repaired hepatocytes will be ascertained by immunohistochemistry for FAH. Mutant hepatocytes do not express any Fah protein. Gene repaired hepatocytes can be readily detected, even as single Fah+ cells.

It is expected that TGF-beta inhibition will enhance the recombination frequency and hence yield higher levels of Fah+ hepatocytes.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A method of increasing the efficiency of genome editing in a human subject in need thereof, the method comprising administering to the human subject an antibody that specifically binds TGFβ or TGFβR1 and that inhibits the expression or activity of TGFβ, wherein the method increases the efficiency of genome editing using a targeted nuclease in the human subject.

2. The method of claim 1, wherein the targeted nuclease is a meganuclease.

3. The method of claim 1, wherein the targeted nuclease is Cas9.

4. The method of claim 1, wherein the targeted nuclease is a zinc finger nuclease.

5. The method of claim 1, wherein the targeted nuclease is a transcription activator like effector nuclease.

6. The method of claim 1, wherein the targeted nuclease is a clustered regularly interspaced short palindromic repeat (CRISPR)-associated nuclease.

7. The method of claim 1, wherein the antibody is administered systemically.

* * * * *